(12) United States Patent
Le Port et al.

(10) Patent No.: US 8,835,695 B2
(45) Date of Patent: Sep. 16, 2014

(54) METHOD FOR OXIDIZING HYDROCARBONS WITH OXYGEN

(75) Inventors: Philippe Le Port, Corbas (FR); Thierry Mante, Lyons (FR)

(73) Assignee: Rhodia Operations, Aubervilliers (FR)

( * ) Notice: Subject to any disclaimer, the term of this patent is extended or adjusted under 35 U.S.C. 154(b) by 0 days.

(21) Appl. No.: 13/516,664

(22) PCT Filed: Dec. 7, 2010

(86) PCT No.: PCT/EP2010/069031
§ 371 (c)(1),
(2), (4) Date: Aug. 28, 2012

(87) PCT Pub. No.: WO2011/073053
PCT Pub. Date: Jun. 23, 2011

(65) Prior Publication Data
US 2012/0310017 A1 Dec. 6, 2012

(30) Foreign Application Priority Data

Dec. 17, 2009 (FR) ..................................... 09 59113

(51) Int. Cl.
*C07C 407/00* (2006.01)
(52) U.S. Cl.
CPC ........... *C07C 407/00* (2013.01); *C07C 2101/14* (2013.01)
USPC ....................................................... 568/570
(58) Field of Classification Search
USPC ....................................................... 568/570
See application file for complete search history.

(56) References Cited

U.S. PATENT DOCUMENTS

| 3,479,394 A | 11/1969 | Brunie et al. |
| 3,510,526 A | 5/1970 | Bonnart et al. |
| 4,877,903 A | 10/1989 | Costantini et al. |
| 2004/0241059 A1 | 12/2004 | Seidlitz et al. |

FOREIGN PATENT DOCUMENTS

| EP | 0031113 A1 | 7/1981 |
| EP | 0579323 A1 | 1/1994 |
| GB | 777087 | 6/1957 |
| GB | 964869 | 7/1964 |
| GB | 1112837 | 5/1968 |
| GB | 1191573 | 5/1970 |
| GB | 1226208 A | 3/1971 |
| JP | s5210865 B1 | 3/1977 |
| JP | H06157456 A | 6/1994 |
| WF | 03031051 A1 | 4/2003 |
| WO | 2006515558 A | 6/2006 |

OTHER PUBLICATIONS

International Search Report issued on Feb. 21, 2011 by the European Patent Office as the International Search Authority in corresponding International Patent Application No. PCT/EP2010/069031, and an English language translation of the Search Report.

*Primary Examiner* — Sikarl Witherspoon
(74) *Attorney, Agent, or Firm* — Dentons US LLP

(57) ABSTRACT

A method for oxidizing saturated hydrocarbons with oxygen, preferably saturated cyclic hydrocarbons such as cyclohexane, to produce alkyl hydroperoxide is described. A method for oxidizing saturated hydrocarbons with oxygen in a plurality of consecutive steps to control the rate of the reaction and obtain a high degree of alkyl hydroperoxide selectivity is also described. The described methods can relate to methods for condensing oxidation gases recovered in an oxidation reactor and recycling thereof.

11 Claims, No Drawings

METHOD FOR OXIDIZING HYDROCARBONS WITH OXYGEN

CROSS-REFERENCE TO PRIOR APPLICATIONS

This application is a National Stage of PCT/EP2010/069031, filed Dec. 7, 2010, and designating the United States (published in French on Jun. 23, 2011, as WO 2011/073053 A1, the title and abstract were published in English), which claims priority of FR 0959113, filed Dec. 17, 2009, each hereby expressly incorporated by reference in its entirety and each assigned to the assignee hereof.

The present invention relates to a process for oxidizing saturated hydrocarbons with oxygen, preferably saturated cyclic hydrocarbons such as cyclohexane, for the production of alkyl hydroperoxide.

More particularly, it relates to a process for oxidizing saturated hydrocarbons with oxygen, the oxidation being carried out in a plurality of successive steps in order to control the progress of the hydrocarbon oxidation reaction and to obtain good alkyl hydroperoxide selectivity.

Thus, the oxidation process may be carried out in a plurality of devices such as a device comprising a plurality of reactors mounted in series or as a cascade or as a partitioned bubble column comprising a plurality of stages defined by plates, or the like. Such an implementation of the oxidation process means that high selectivity for alkyl hydroperoxide can be obtained.

This oxidation step often forms the first step of a process for producing oxidized compounds such as ketones, alcohols, aldehydes and acids. Thus, the oxidation of cyclohexane by oxygen to form cyclohexyl hydroperoxide is the first step in the process for producing cyclohexanol and cyclohexanone, which may themselves be intermediates in a synthesis, for example that of adipic acid or epsilon-caprolactam.

One of the most widely used industrial processes for producing adipic acid consists of oxidizing cyclohexane with molecular oxygen to cyclohexyl hydroperoxide in the presence or absence of a catalyst, then of catalytically decomposing the hydroperoxide to a mixture of cyclohexanone and cyclohexanol. The ketone and alcohol mixture is then oxidized to adipic acid with nitric acid.

The first step for oxidizing cyclohexane is generally carried out in a biphase gas/liquid medium; the oxidizing gas, namely oxygen or an oxygen-containing gas, is introduced into the liquid medium into reactors constituted by one or more partitioned or non-partitioned bubble columns, mounted in series when one or more is used, functioning either in co-current or in counter-current mode with respect to the direction of movement of the liquid phase principally constituted by cyclohexane in the liquid state. This step is described in particular in patents GB 777087, 1112837, 964869, 1191573, U.S. Pat. No. 3,479,394 and U.S. Pat. No. 4,877,903.

The liquid reaction medium containing the oxidized products, principally alkyl hydroperoxide, is generally recovered from the head of each reactor.

Each reactor also contains at least one gaseous phase forming the "overhead" of the reaction zone.

Carrying out the reaction with a low degree of conversion of the hydrocarbon in each reactor or compartment in order to have a low concentration of oxidized products in the reaction medium favours the production of a suitable yield of and selectivity for alkyl hydroperoxide. To this end, the release of heat induced by the reaction must be controlled.

A high concentration of oxidized products accelerates the reaction rate and degrades its selectivity for upgradable products such as: alkyl hydroperoxide, alcohol, ketone. A lack of control of the temperature also accelerates the reaction rate and encourages deperoxidation of the alkyl hydroperoxide.

For this reason, in order to obtain a degree of alkyl hydroperoxide production which is compatible with industrial operation, the oxidation reaction is generally carried out in several reactors mounted in series or in a cascade or in a bubble column partitioned by the presence of plates, or the like.

In such a process, it is important to control, on the one hand, the temperature in each reactor or each compartment in order to maintain the reaction medium in the optimal domain, and on the other hand to control the concentration of oxidized products in the reaction medium. This regulation may, for example, be obtained by supplying the hydrocarbon at a lower temperature to one or more reactors or compartments, especially the last reactors of the cascade or the last compartments of the column.

For process cost reasons, it is also important to recover the gaseous phase forming the overhead of the reactors or compartments and to recycle the products present in these gaseous phases, such as non-oxidized hydrocarbon, and oxidized products such as hydroperoxides, alcohols and ketones. However, recycling such recovered products must not perturb or diminish the performances of the process and in particular the operating conditions of the reactor or compartment in which said recycle takes place.

One of the aims of the present invention is to propose a process for oxidizing a saturated hydrocarbon implemented in a device for carrying out oxidation in a plurality of successive steps such as, for example, a plurality of reactors mounted in series or one or more partitioned bubble columns and comprising a process for recovering and recycling gaseous phases forming the overhead of the reactors or compartments of the column which has many advantages as regards the overall costs of the process.

To this end, the invention proposes a process for oxidizing a saturated hydrocarbon with oxygen in order to produce an alkyl hydroperoxide. This process consists of bringing a hydrocarbon in the liquid phase into contact with oxygen or an oxygen-containing gas, said reaction being carried out in a plurality of successive steps. In such a process, the saturated hydrocarbon is supplied to at least the first step at a temperature in the range 100° C. to 250° C., preferably in the range 150° C. to 200° C. when the reaction is carried out in the absence of catalyst. Furthermore, at least in the last step, the reaction medium is cooled in order to maintain the temperature of the reaction medium at a level less than or equal to that of the first step in order to obtain a suitable selectivity for alkyl hydroperoxide. Preferably, at least in the last step, the reaction medium is cooled in order to maintain the temperature of the reaction medium at a level below that of the first step.

The process of the invention is characterized in that the gaseous phases forming the overhead in each step of the reaction are recovered and at least partially condensed, either separately or after mixing the gaseous phases derived from several reaction steps. The condensate or condensates obtained are recycled to at least one step wherein the concentration of oxidized products in the reaction medium supplied to said step is at least equal to the concentration of oxidized products contained in the condensate or condensates to be recycled. Preferably, the condensate or condensates obtained are recycled directly into at least one step wherein the concentration of oxidized products in the reaction medium supplied to said step is at least equal to the concentration of oxidized products contained in the condensate or condensates to be recycled. The term "directly" as used in the context of the present invention means that the condensate or condensates do not undergo any intermediate purification treatment, in particular distillation.

In accordance with one implementation of the invention, the gaseous phase recovered at the head of one reaction step is partially condensed and the condensate obtained is recycled to the supply to the preceding step.

Hence in particular, the gaseous phase recovered at the head of the last reaction step is partially condensed, and the condensate obtained is advantageously recycled to one of the steps located upstream, in particular to the supply to the preceding step.

Recycling said condensate can in particular control and maintain the temperature in said reaction step within the optimal range described above and without increasing the concentration of oxidized products in the reaction medium. The temperature of these condensates is lower than that of the reaction medium present in said step and thus allows the temperature to be maintained within a range reducing the rate at which the oxidation reaction progresses and thus can improve the selectivity for alkyl hydroperoxide. That selectivity in fact decreases very rapidly with the degree of progress of the reaction. The optimal temperature range is determined in order to have a minimal autocatalytic effect on the reaction.

In known processes, this control of the temperature is generally achieved by supplying cold hydrocarbon to said step. Sources of cold hydrocarbons which are available are constituted by distillates ensuring the recycling of untransformed hydrocarbon downstream of the process. Thus, this cold hydrocarbon is a product purified by distillation.

With the process of the invention, the quantity of recycled and purified hydrocarbon which has to be supplied to said step is greatly reduced, and in some cases may even be reduced to zero.

Furthermore, the supplied recycled and purified cold hydrocarbon could maintain the concentration of oxidized products in said step at a value below a critical value for the selectivity and the reaction rate.

This effect is also obtained by recycling the condensates in accordance with the invention, since these condensates have a concentration of oxidized products that is at most equal to that present in the reaction medium supplied to said step, and thus means that the concentration of oxidized products in said step can be controlled.

Furthermore, the heavy products present in the gaseous phases are condensed and thus recycled solely to the last steps of the reaction. Thus, the oxidation reaction is carried out in the first steps with a low concentration of heavy products. This low concentration can also improve the overall selectivity of the reaction.

Thus, the process of the invention means that the quantity of recycled and purified hydrocarbon used to cool the reaction media in certain steps of the reaction can be reduced. This purified hydrocarbon can thus be directly supplied to the first step of the oxidation reaction, improving the selectivity of the reaction and the process costing.

Furthermore, the gaseous phases or condensates recycled to the first steps of the process contain little of the products known as "heavy" products, which also means that the selectivity for hydroperoxide of the oxidation reaction can be improved.

Since the overall selectivity is improved, the quantity of hydrocarbon consumed per tonne of cyclohexanol and cyclohexanone is reduced.

In one implementation of the invention, it is advantageous to recover and mix the gaseous phases forming the overhead from several steps of the oxidation reaction and to mix them before partially condensing them. The recovered condensate is advantageously recycled to one of the steps wherein the concentration of oxidized products in the supplied reaction mixture is greater than or equal to that in the condensate to be recycled.

However, all possible combinations and associations of the recovered gaseous phases are encompassed within the scope of the invention.

Furthermore, it is also possible to condense each gaseous phase separately and to recycle the various condensates obtained in a separate manner or after having mixed them or having produced mixtures of certain of them.

In accordance with one feature of the invention, the suitable saturated hydrocarbons of the invention are advantageously saturated cyclic hydrocarbons such as cyclohexane, cyclooctane, cyclododecane or decalin. Preferably, the saturated hydrocarbon suitable for the invention is cyclohexane.

Cyclohexane is the hydrocarbon used for the production of cyclohexyl hydroperoxide, an intermediate in the production of cyclohexanone and/or cyclohexanol in particular. This alcohol/ketone mixture is, for example, used for the synthesis of adipic acid by nitric oxidation.

In the case of the oxidation of cyclohexane without a catalyst, the gaseous phases recovered in the various steps of the reaction are advantageously partially condensed at a temperature which is higher than the condensation temperature of formic acid. This acid, which is formed during the oxidation step, is deleterious to the selectivity of the reaction as it catalyses deperoxidation of the hydroperoxide.

In accordance with another characteristic of the invention, the gas fractions recovered after partial condensation of the gaseous phases recovered at the outlet from the various steps and the recycles of the condensed phases or condensates to the various oxidation steps undergo a total, second condensation. The condensate is then flashed to recover, in addition to non-condensables, an organic phase which is advantageously recycled to the first oxidation step, advantageously after mixing with the recycled hydrocarbon deriving from the various distillations downstream of oxidation, and an aqueous phase constituted by the water formed during the oxidation containing the great majority of the formic acid. This aqueous phase is advantageously destroyed by incineration, for example.

The term "oxidized products" means the compounds obtained by hydrocarbon oxidation and comprising oxygen atoms. These products are alkyl hydroperoxides, alcohols, ketones, aldehydes, acids and the like in particular.

The process of the invention can be used to produce an alkyl hydroperoxide, especially cyclohexyl hydroperoxide, in a suitable yield, and with a consumption of cyclohexane per tonne of cyclohexanol and cyclohexanone produced which is lower than that observed when the recycle of the condensates derived from the gaseous phases forming the overhead from the various oxidation steps employed in accordance with the process of the invention is replaced by a makeup of recycled and purified cold cyclohexane downstream of the oxidation step.

The process of the invention may be carried out continuously in various types of plant, as will be described below. The number of reactors and the reactor type used are not critical to the invention.

In accordance with a preferred characteristic of the invention, preferred types of plant are a plant comprising an oxidation reactor constituted by a bubble column partitioned by plates or a plant comprising several oxidation reactors mounted as a cascade or in series, each reactor possibly being of the bubble column type. Thus, each space defined by two adjacent plates or each reactor corresponds to one step of the oxidation reaction. The number of plates in a column or the number of reactors forming a reactor cascade may vary and may advantageously be in the range 3 to 10.

Other details and advantages of the invention will become more apparent from the examples given below purely by way of illustration.

COMPARATIVE EXAMPLE NO 1

In a plant for the oxidation of cyclohexane to cyclohexyl hydroperoxide comprising a cascade of n bubble column type reactors with a co-current supply of oxidizing gas (air) and reaction medium to be oxidized, a stream of hot cyclohexane was supplied to the first reactor of the column at a temperature of 182° C. The hot stream of cyclohexane contained 0.31% by weight of cyclohexyl hydroperoxide, cyclohexanol and cyclohexanone.

The oxidation reaction was carried out without a catalyst. The liquid reaction medium leaving one reactor was supplied to the next reactor in the cascade. The gaseous phases or oxidation gas from each reactor were recovered and condensed, certain of them after mixing.

The temperature in the last reactor n of the cascade was 180° C. In order to maintain the temperature at that value, "cold" cyclohexane, at 70° C., was supplied, as a complement to the reaction medium, to the last two reactors, n and n−1, of the cascade. The stream of "cold" cyclohexane supplied to each reactor represented 8.3% by weight of the stream of "hot" cyclohexane supplied to the first reactor of the cascade.

At the outlet from the last oxidation reactor, a portion of the unreacted cyclohexane was separated from the reaction mixture for recycling to the oxidation step. The reaction mixture was then washed with water, and treated with a catalyst in order to transform the cyclohexyl hydroperoxide to cyclohexanol and cyclohexanone. The cyclohexane was then separated by distillation, and the impure cyclohexanol—cyclohexanone was purified by distillation.

The oxidation gases were mixed and condensed in a condenser train. The liquid fraction recovered was flashed. The organic phase recovered after water separation was recycled in the cyclohexane supplied to the first reactor of the cascade before the cyclohexane heating step.

EXAMPLE 1, IN ACCORDANCE WITH THE INVENTION

The process of Example 1 was carried out in the plant described in the comparative example, using the same reagents.

However, in accordance with the invention, the oxidation gases or gaseous phase recovered in the last reactor n of the cascade were condensed separately. The condensate thus recovered was at a temperature of 145° C., representing 4.5% of the flow of the hot cyclohexane supplied to the first reactor, mixed with the reaction medium supplied to reactor n−1 as a complement to and partial replacement for the "cold" cyclohexane supplied to this reactor.

The oxidation gases or gaseous phases from the other reactors were mixed and condensed. The least volatile fraction of these condensates, recovered at a temperature of 125° C., representing 11.5% of the flow of the hot cyclohexane supplied to the first reactor, was recycled to the reaction medium entering the reactor n−2. The remainder of the condensates was treated in a similar manner to that described in the comparative example above. The organic phase which was finally recovered was mixed with cyclohexane resulting from the various recycles downstream of the oxidation, before heating said cyclohexane for supply to the first reactor of the cascade.

With the recycle of at least a portion of the condensates as described above, the "hot" cyclohexane supplied to the first reactor contained 0.19% by weight of cyclohexyl hydroperoxide, cyclohexanol and cyclohexanone. The temperature in the first reactor was equal to 185° C.; the temperature of the last reactor remained at 180° C.

The flows of "cold" cyclohexane supplied to the last two reactors of the cascade respectively represented 6.5% and 5.5% of the flow of the hot cyclohexane supplied to the first reactor.

The selectivity of the cyclohexanol and cyclohexanone production process calculated after the step for transformation of the cyclohexyl hydroperoxide increased by 1%. The selectivity represents the percentage of cyclohexane consumed and transformed into cyclohexanol and cyclohexanone. This gain in selectivity for cyclohexanol and cyclohexanone was essentially obtained by reducing the concentration of oxidized products in the hot cyclohexane supplied to the first reactor of the cascade.

COMPARATIVE EXAMPLE NO 2

In another plant for the oxidation of cyclohexane to cyclohexyl hydroperoxide comprising a cascade of n bubble column type reactors with a co-current supply of oxidizing gas (air) and reaction medium to be oxidized, a stream of hot cyclohexane was supplied to the first reactor of the column at a temperature of 185° C. The stream of hot cyclohexane contained 0.20% by weight of cyclohexyl hydroperoxide, cyclohexanol and cyclohexanone.

The oxidation reaction was carried out without a catalyst. The liquid reaction medium leaving one reactor was supplied to the next reactor in the cascade. The gaseous phases or oxidation gases from each reactor were recovered and condensed, some of them after mixing.

The temperature in the last reactor n of the cascade was 179° C. In order to maintain the temperature at this value, "cold" cyclohexane, at 70° C., was supplied, as a complement to the reaction medium, to the last three reactors n−2, n−1 and n of the cascade. The stream of "cold" cyclohexane supplied to each reactor represented 2.7%, 3.1% and 2.7% by weight of the stream of "hot" cyclohexane supplied to the first reactor of the cascade, i.e. 8.5% in total.

At the outlet from the last oxidation reactor, a portion of the unreacted cyclohexane was separated from the reaction mixture for recycling to the oxidation step. The reaction mixture was then washed with water and treated with a catalyst in order to transform the cyclohexyl hydroperoxide into cyclohexanol and cyclohexanone. The cyclohexane was then separated by distillation, and the impure cyclohexanol—cyclohexanone mixture was purified by distillation.

The oxidation gases were mixed and condensed in a condenser train. The liquid fraction recovered was flashed. The organic phase recovered after water separation was recycled to the cyclohexane supplied to the first reactor of the cascade before the cyclohexane heating step.

EXAMPLE 2, IN ACCORDANCE WITH THE INVENTION

The process of Example 2 was carried out in the plant described in comparative Example 2, using the same reagents.

The oxidation gases or gaseous phases from the first n−1 reactors were mixed and condensed. The least volatile fraction of these condensates, recovered at a temperature of 125° C., representing 8.1% of the flow of the hot cyclohexane supplied to the first reactor, was recycled to the reaction medium entering the reactor n−2. The remainder of the condensates was treated in a manner similar to that described in the comparative example above. The organic phase finally recovered was mixed with cyclohexane resulting from the various recycles downstream of the oxidation, before heating said cyclohexane for supply to the first reactor of the cascade.

With the recycle of at least a portion of the condensates as described above, the "hot" cyclohexane supplied to the first reactor contained 0.16% by weight of cyclohexyl hydroperoxide, cyclohexanol and cyclohexanone. The ethylene in the first reactor was equal to 186.5° C.; the temperature in the last reactor remained at 179° C.

"Cold" cyclohexane was supplied to the reactors n−3, n−2, n−1 and n of the cascade at respective flows of 1%, 0.5%, 2.7% and 1.6% of the flow of the hot cyclohexane supplied to the first reactor, i.e. 5.8% in total.

The selectivity of the process for cyclohexanol and cyclohexanone, calculated after the step for transformation of the cyclohexyl hydroperoxide, was increased by 0.6%. The selectivity represents the percentage of cyclohexane consumed and transformed into cyclohexanol and cyclohexanone. This gain in selectivity for cyclohexanol and cyclohexanone was essentially obtained by reducing the concentration of oxidized products in the hot cyclohexane supplied to the first reactor of the cascade.

The invention claimed is:

1. A process for producing alkyl hydroperoxide, the process comprising oxidizing a saturated hydrocarbon in a liquid phase with an oxygen-containing gas, and conducting the oxidation in a plurality of successive steps, comprising supplying hydrocarbon at least to a first step at a temperature of from 100° C. to 250° C., further comprising cooling in, at least a last step of the reaction to maintain and control temperature at a level which is less than or equal to a temperature used in the first step, wherein each step of the reaction comprises a liquid phase and a gaseous phase and comprises forming a gaseous overhead extracting and evacuating the gaseous phase forming the overhead to be at least partially condensed, and recovering at least one condensate from the gaseous phase of one step and recycling the condensate directly into one of the oxidation steps, wherein a resulting concentration of oxidized products in the supplied reaction medium is at least equal to a concentration of oxidized products in the condensate or condensates to be recycled.

2. The process as defined by claim 1, wherein the condensate recycled to one step is obtained by mixing condensates or gaseous phases deriving from at least two oxidation steps.

3. The process as defined by claim 1, wherein the gaseous phase recovered at a head of one reaction step is partially condensed and the condensate obtained is recycled to a supply to the preceding step.

4. The process as defined by claim 1, wherein the gaseous phase recovered at a head of the last reaction step is partially condensed and the condensate obtained is recycled to a supply to the preceding step.

5. The process as defined by claim 1, wherein the saturated hydrocarbon is a cyclic hydrocarbon.

6. The process as defined by claim 5, wherein the saturated hydrocarbon is selected from the group consisting of cyclohexane, cyclooctane, cyclododecane and decalin.

7. The process as defined by claim 6, wherein the saturated hydrocarbon is cyclohexane.

8. The process as defined by claim 1, wherein after partial condensation of the gaseous phases forming the overhead of each step, the process further comprises completely condensing any uncondensed fraction, then flashing a condensate obtained in order to obtain an aqueous liquid fraction and an organic fraction, and recycling said organic fraction to the first oxidation step.

9. The process as defined by claim 1, wherein the oxidation is carried out in a plant comprising a plurality of oxidation reactors mounted in series or as a cascade, each reactor forming an oxidation step.

10. The process as defined by claim 9, wherein the reactors are of a bubble column type.

11. The process as defined by claim 1, wherein oxidation is carried out in a plant comprising as an oxidation reactor a partitioned bubble column, each compartment forming an oxidation step.

* * * * *